(12) United States Patent
Motouchi

(10) Patent No.: US 6,769,420 B1
(45) Date of Patent: Aug. 3, 2004

(54) IONIZER

(75) Inventor: Kazuo Motouchi, Kobe (JP)

(73) Assignees: Satoko Fujiwara, Hyogo (JP); Kyoko Motouchi, Hyogo (JP)

( * ) Notice: Subject to any disclaimer, the term of this patent is extended or adjusted under 35 U.S.C. 154(b) by 0 days.

(21) Appl. No.: 09/979,081

(22) PCT Filed: Mar. 27, 2000

(86) PCT No.: PCT/JP00/01883

§ 371 (c)(1),
(2), (4) Date: Nov. 16, 2001

(87) PCT Pub. No.: WO01/73908

PCT Pub. Date: Oct. 4, 2001

(51) Int. Cl.$^7$ ............................................... H01J 27/02
(52) U.S. Cl. ....................................................... 123/539
(58) Field of Search ................................ 123/536, 537, 123/538, 539

(56) References Cited

U.S. PATENT DOCUMENTS

| | | | | |
|---|---|---|---|---|
| 3,943,407 A | * | 3/1976 | Bolasny | 123/539 |
| 5,010,869 A | * | 4/1991 | Lee | 123/539 |
| 5,977,716 A | * | 11/1999 | Motouchi | 123/537 |
| 6,176,977 B1 | * | 1/2001 | Taylor et al. | 123/539 |
| 6,536,418 B1 | * | 3/2003 | Ling | 123/539 |

FOREIGN PATENT DOCUMENTS

| | | |
|---|---|---|
| JP | 56-162257 | 12/1981 |
| JP | 59-16556 | 1/1984 |
| JP | 59-195503 | 11/1984 |
| JP | 63-192950 | 8/1988 |
| JP | 1-114049 | 8/1989 |
| JP | 2-9461 | 1/1990 |
| JP | 2-296704 | 12/1990 |
| JP | 5-15577 | 1/1993 |
| JP | 6-325892 | 11/1994 |
| JP | 6-325893 | 11/1994 |
| JP | 8-86512 | 4/1996 |
| JP | 8-138829 | 5/1996 |
| JP | 9-184455 | 7/1997 |
| JP | 10-34015 | 2/1998 |
| JP | 10-314289 | 12/1998 |

* cited by examiner

Primary Examiner—Marguerite McMahon

(57) ABSTRACT

An ionization electrode consists of a plate-like positive pole (31a) formed with plural pointed ends (31b) on its outer edge, and a spheric negative pole (32a) opposing a flat surface of the positive pole (31a). Since the pointed ends (31b) of the positive pole (31a) are not in direct face-to-face relation with the negative pole (32a), corona discharge is prevented from concentrating on some of the pointed ends (31b) that are closer to the negative pole (32b) than the rest due to the working errors or mounting errors of the poles. Therefore, the corona discharge occurs in a stable manner.

7 Claims, 8 Drawing Sheets

IONIZER

FIELD OF THE INVENTION

The present invention relates to an ion generator adapted to generate ozone by ionizing air introduced into a casing.

DESCRIPTION OF THE PRIOR ART

There have been used ion generators designed to supply ionized air to intake manifolds of internal combustion engines for the purposes of enhancing the combustion efficiency thereof, improving the fuel economy and reducing the air pollution.

FIG. 10 is a sectional view showing an exemplary prior-art ion generator. A casing 80 of this ion generator includes a cylinder body 89 which is formed from stainless steel or the like and the opposite ends of which are closed by caps 84, 85. One 84 of the caps is formed with an intake port 86 whereas the other cap 85 is formed with an exhaust port 87. The ion generator has an arrangement wherein a gap between the intake port 86 and the exhaust port 87 defines an air-flow passage A in which a high-voltage generator 88 is disposed on an upstream side and an ionization electrode I is disposed on a downstream side.

The ionization electrode I includes an outside electrode 81 formed by a part of the cylinder body 89, an inside electrode 82 disposed centrally of the outside electrode 81, and a pair of disk-like support members 83 for supporting the inside electrode 82. The inside electrode 82 includes a conductive shaft 82a bridging the pair of support members 83, and a plurality of star electrodes 82b axially mounted on the conductive shaft 82a at regular space intervals. The inside electrode 82 is connected to one pole of the high-voltage generator 88 while the outside electrode 81 is connected to the other pole of the high-voltage electrode 88.

The pair of support members 83 are formed from an insulating material. The support members are each formed with vent holes 83c extended through a side thereof and arranged at given space intervals along a circumference about the shaft 82a such that the air introduced into the casing 80 through the intake port 86 is guided to the exhaust port 87 by the vent holes.

In the ion generator, a high voltage is applied between the outside electrode 81 and the inside electrode 82 of the ionization electrode I for effecting corona discharge therebetween such that the air in the electrode is ionized to produce ozone.

Unfortunately, the ionization electrode I of FIG. 10 suffers a poor air-ionization efficiency because a majority of the corona discharge develops from the star electrodes 82b at the opposite ends of the shaft 82a while the other star electrodes 82b between these electrodes do not function effectively. The ionization electrode also suffers the following problem. If the star electrodes are eccentric with respect to the outside electrode 81 due to the working errors or mounting errors of the outside electrode 81 and the inside electrode 82, the corona discharge will concentrate on some of the pointed ends of the star electrodes 82b that are the closest to the outside electrode 81, thus developing into spark discharge, which will cause burn of an electric circuit component and the like of the high-voltage generator 88. Furthermore, even if the discharge does not concentrate on one place, there occurs an instable corona discharge rather closer to the spark discharge. Hence, a measure must be taken to provide the stable discharge by increasing the current value of a primary winding of a transformer incorporated in the high-voltage generator 88. This results in an increased power consumption.

FIG. 11 is a sectional view showing an ionization electrode D of another prior-art ion generator.

A casing 90 of the ionization electrode D includes a cylinder body 91 formed from a resin material and a pair of closure plates 92 for closing opposite ends of the cylinder body 91, the closure plate formed with a plurality of vent holes 92a.

The ionization electrode D includes a hollow brass electrode 93 attached to one of the closure plates 92 of the casing 90, and a spherical electrode portion 94 attached to the other closure plate 92. The spherical electrode portion 94 consists of a spherical electrode 94a and a support member 94b. A plurality of rectangular fins 93a formed from a thin stainless-steel sheet are attached to an outer periphery of a distal end of the hollow electrode 93, the fins arranged with equal spacing.

The ionization electrode D operates as follows. A DC positive high voltage is applied between the hollow electrode 93 and the spherical electrode portion 94 while allowing for an air flow from the hollow electrode 93 to the spherical electrode portion 94, thereby effecting corona discharge B from end faces of the fins 93a toward the spherical electrode 94a, the end faces opposing the spherical electrode portion 94. The air within the electrode D is ionized by the corona discharge B to produce ozone.

The ionization electrode D of FIG. 11 involves a cumbersome working of the fins 93a, which are insufficient in the ability to generate discharge unless they are so thin as about 0.1 mm. In addition, this electrode also suffers the same drawbacks as the ionization electrode I of FIG. 10. That is, the discharge concentrates on one place due to the working errors or mounting errors of the electrodes, resulting in the burn of the electric circuit component and the like. Even if the discharge does not concentrate on one place, the current value of the primary winding of the transformer must be increased and hence, an increased power consumption results.

Accordingly, it is an object of the invention to provide an ion generator adapted for stable generation of corona discharge despite the working errors or mounting errors of the electrodes.

It is another object of the invention to provide an ion generator allowing for the reduction of the current value of the primary winding of the transformer thereby achieving the reduction of power consumption.

It is still another object of the invention to provide an ion generator adapted to improve the air ionization efficiency.

DISCLOSURE OF THE INVENTION

An ion generator according to the invention for achieving the above objects comprises a casing having an intake port and an exhaust port; an ionization electrode contained in the casing and including a first plate-like pole having a plurality of pointed ends at least on a part of its edge and a second pole opposing a flat surface of the first pole; and a high-voltage generator for applying a high voltage to the ionization electrode (claim 1).

According to the ion generator of this arrangement, the discharge is prevented from concentrating on some of the pointed ends of the first pole that are closer to the second pole than the rest due to the working errors or mounting errors of the poles. This is presumed to be the result of the arrangement wherein the second pole in the ionization electrode opposes the flat surface of the first pole or the first pole does not present its pointed ends directly to the second pole. That is, the corona discharge has a lower directivity than in the arrangement wherein the pointed ends of the first pole are in direct face-to-face relation with the second pole. Accordingly, the corona discharge occurs in a stable manner free from the fear of developing into the spark discharge. Thus, the ion generator of the invention eliminates the possibility of troubles such as the burn of the electric circuit component of the high-voltage generator. Furthermore, the inventive ion generator is adapted to save power by reducing the current value of the primary winding of the transformer and to improve the air ionization efficiency.

According to one preferred mode of the invention, the ion generator has an arrangement wherein the second pole has a discharge surface three-dimensionally curved into a convex surface (claim 2). The ion generator features a further lowered directivity of the corona discharge. This leads to an even greater effect to prevent the discharge from concentrating on some of the pointed ends due to the working errors or mounting errors of the poles, ensuring a more stable corona discharge. As a result, the current value of the primary winding of the transformer can be further decreased while the air ionization efficiency is further increased.

It is preferred in the ion generator that the first pole comprises a star electrode whereas the second pole has a spheric discharge surface (claim 3). This arrangement also ensures a more stable generation of corona discharge.

The ion generator may have an arrangement wherein the second pole comprises a flat plate inclined at a predetermined angle relative to the flat surface of the first pole (claim 4). The arrangement provides an even greater effect to prevent the discharge from concentrating on some of the pointed ends due to the working errors or mounting errors of the poles. This eliminates the fear that the corona discharge may develop into the spark discharge, ensuring the stable generation of corona discharge.

Another ion generator according to the invention comprises a casing having an intake port and an exhaust port; an ionization electrode contained in the casing and including a first plate-like pole having a plurality of sawtooth-like pointed ends arranged linearly, and a second pole having a discharge surface defined by a cylinder or a part thereof and its generatrix extended in parallel with the pointed ends of the first pole; and a high-voltage generator for applying a high voltage to the ionization electrode (claim 5). In this ion generator as well, the first pole does not present its pointed ends directly to the second pole whereas the discharge surface of the second pole is in the form of a convex surface defined by a cylinder or a part thereof. Hence, the directivity of the corona discharge is presumed to be lowered so that the corona discharge occurs in a stable manner as prevented from concentrating on some of the pointed ends due to the working errors or mounting errors of the poles. Accordingly, the current value of the primary winding of the transformer can be reduced for power saving while the air ionization efficiency can be increased. In addition, the elongated first and second poles are able to generate a large quantity of corona discharge at a time, thereby producing a large quantity of ozone.

According to one preferred mode of the invention, the ion generator has an arrangement wherein the first poles are disposed at plural places arranged peripherally of the second pole as presenting their respective flat surfaces to a peripheral surface of the second pole (claim 6). This arrangement provides an even greater ozone generation.

The ion generator may have an arrangement wherein the first pole is formed with plural lines of pointed *z ends whereas the second pole is disposed in correspondence to each of the lines of pointed ends (claim 7). This arrangement also provides a greater ozone generation.

It is preferred in the inventive ion generator that the first pole is formed from tungsten (claim 2). In this case, the pointed ends of the first pole resist oxidation by ozone even if they are heated to about 1000° C. by the corona discharge so generated and hence, the subsequent generation of corona discharge will not be obstructed. In addition, tungsten does not act as a catalyst assisting the reaction of ozone on the surface of the first pole.

The ion generator of the invention may be provided in an air charging system for supplying air to an internal combustion engine (claim 3). In this case, a highly efficient combustion of the internal combustion engine is ensured.

The ion generator of the invention may have an arrangement wherein the intake port of the casing is provided with a dust filter whereas the exhaust port is provided with a silocco fan for discharging ionized air (claim 4). In this case, air filtered by the dust filter may be continuously introduced into the casing, efficiently ionized and discharged out of the casing. This provides for an efficient supply of ozone to a combustion apparatus such as a boiler, incinerator or the like.

The ion generator of the invention may have an arrangement wherein the intake port of the casing is provided with a dust filter whereas the exhaust port is provided with an air pump for discharging ionized air (claim 5). In this case as well, the air filtered by the dust filter may be continuously introduced into the casing, efficiently ionized and discharged out of the casing.

The ion generator of the invention may further comprise a solar panel for converting the radiation energy of the solar light to an electrical energy, and a power source section comprising a storage battery for storing the electrical energy (claim 6). In this case, the ion generator is portable because the current for corona discharge is supplied from the power source section. Equipped with the solar panel and designed for automatic storage of the electrical energy, the ion generator can be used for an extended period of time without recharging from utility power.

BEST MODES FOR CARRYING OUT THE INVENTION

Next, preferred embodiments of the invention will be described with reference to the accompanying drawings.

Figure 1:
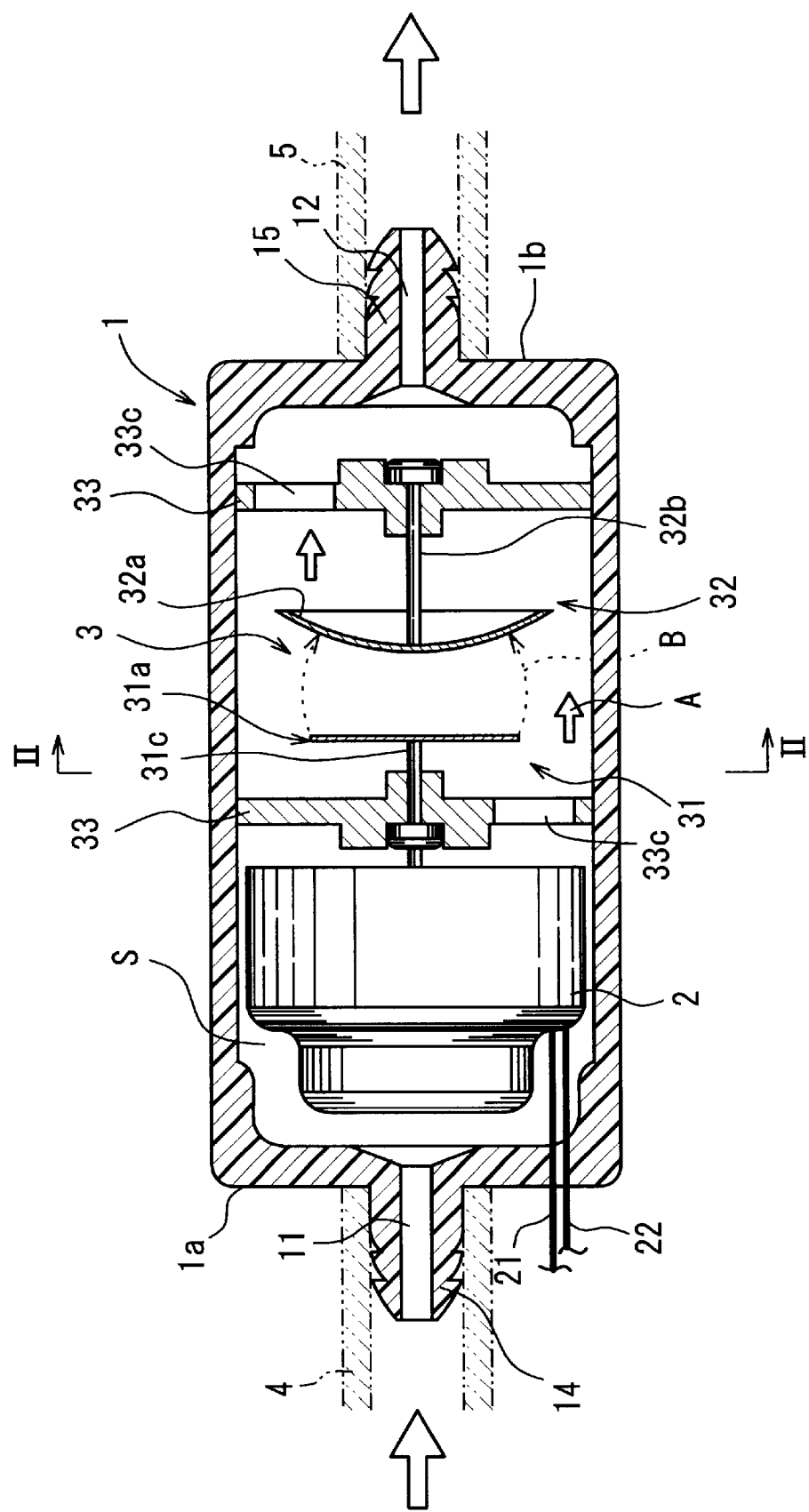
FIG.1 is a sectional view showing an ion generator according to a first embodiment of the invention.
Figure 2:
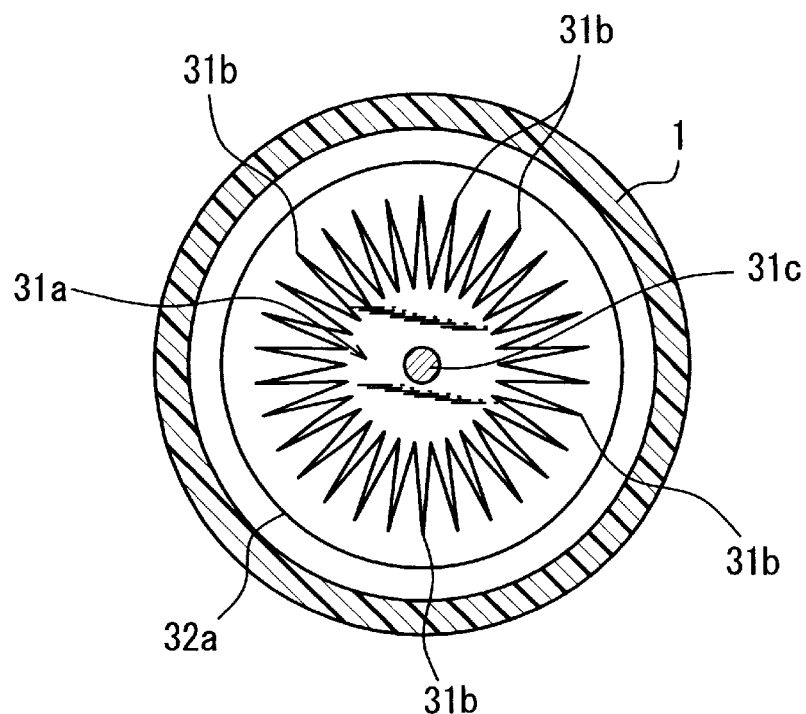
FIG. 2 is an enlarged sectional view taken on the line II—II in FIG. 1.

FIG. 1 is a sectional view showing an ion generator according to a first embodiment of the invention, whereas FIG. 2 is an enlarged sectional view thereof taken on the line II—II in FIG. 1.

The ion generator is designed to ionize air for supplying the ionized air to an intake manifold interposed between an air cleaner and a cylinder within an internal combustion engine.

In the ion generator, a cylindrical casing 1 is formed with an intake port 11 at one end 1a thereof and with an exhaust port 12 at the other end 1b thereof. A space between the intake port 11 and the exhaust port 12 defines an air-flow passage A. A high-voltage generator 2 is disposed on an upstream side of the air-flow passage A, whereas an ionization electrode 3 is disposed on a downstream side thereof.

The casing 1 is formed from a synthetic resin, such as polyetherimde, having a connection port 14 for an intake pipe 4 protruded from one end 1a thereof and a connection port 15 for an exhaust pipe 5 protruded from the other end 1b thereof. The intake port 11 and the exhaust port 12 are coaxial with the casing 1. The exhaust pipe 5 communicates with the intake manifold.

The high-voltage generator 2 has an arrangement wherein an electric circuit component including a transformer for high-voltage generation is housed in a case and molded therein by an epoxy resin or the like. The high-voltage generator 2 is positioned neutrally of the casing 1 as supported by ribs projecting from plural places of an outer periphery thereof, so that a gap S is defined along its outer peripheral surface and its end opposite the intake port 11 for allowing the air introduced into the casing 1 through the intake port 11 to flow therethrough. The high-voltage generator 2 is disposed coaxially with the intake port 11 and the exhaust port 12. In the figure, the reference numeral 21 denotes a power cable whereas the numeral 22 denotes a ground lead.

The ionization electrode 3 includes (1) a positive pole portion 31 including a positive pole (a first pole) 31a of a thin star shape formed with pointed ends 31b on its outer circumference, and a support shaft 31c; (2) a negative pole portion 32 including a negative pole (a second pole) 32a in opposed relation with a flat surface of the positive pole 31a, and a support shaft 32b; and (3) and a pair of disk-like support members 33 supporting the positive pole portion 31 and the negative pole portion 32, respectively. The pointed end 31b is in the form of an equilateral triangle.

The positive pole 31a is connected to one pole of the high-voltage generator 2 while the negative pole 32a is connected to the other pole of the high-voltage generator 2. In the ionization electrode 3, the negative pole 32a is grounded and a positive high voltage from the high-voltage generator 2 is applied between the positive pole 31a and the negative pole 32a. The positive pole 31a is formed from tungsten, which eliminates a fear that the pointed ends 31b may be oxidized by ozone and which does not act as a catalyst assisting the reaction of ozone on the surface of the positive pole 31a. The negative pole 32a is formed of a stainless steel sheet three-dimensionally curved into a convex surface, or defined by a part of a spheric surface.

The pair of support members 33 are formed from an insulating material such as a diallyl phthalate resin, phenol resin, epoxy resin or the like, each having one vent hole 33c extended through its side for guiding the air, introduced into the casing 1 through the intake port 11, to the exhaust port 12.

The above arrangement allows a negative pressure in the intake manifold to introduce the air into the casing 1 through the intake port 11 and to move the introduced air through the gap S between the high-voltage generator 2 and the casing 1 to the exhaust port 12. In this process, the air having passed the high-voltage generator 2 is ionized by corona discharge from the ionization electrode 3 and the air thus ionized is supplied to the intake manifold through the exhaust port 12 and the exhaust pipe 5.

In this embodiment, the pointed ends 31b on the outer circumference of the positive pole 31a emits the corona discharge B along arcuate paths to the negative pole 32a, the arcuate paths indicated by the dot lines in FIG. 1. This ion generator features the positive pole 31a with the pointed ends 31b radially extended toward an inner circumference of the casing 1 or not in direct face-to-face relation with the negative pole 32a. As combined effects of this configuration and the convex surface of the negative pole 32a, the corona discharge B is presumed to be lowered in directivity. Therefore, the discharge is prevented from concentrating on some of the pointed ends 31b that are closer to the negative pole 32a than the rest because of the working errors or mounting errors of the positive pole 31a and the negative pole 32a. This permits the corona discharge B to be generated in such a stable manner free from the fear of developing into the spark discharge. As a result, the high-voltage generator 2 is free from troubles including the burn of the electric circuit component and the like. Furthermore, a current value of a primary winding of the transformer can be reduced to about ⅓ of that of the prior-art arrangement, so that the ion generator can save power. In addition, the ion generator can generate an increased quantity of ozone per unit time, achieving an efficient air ionization.

Figure 4:
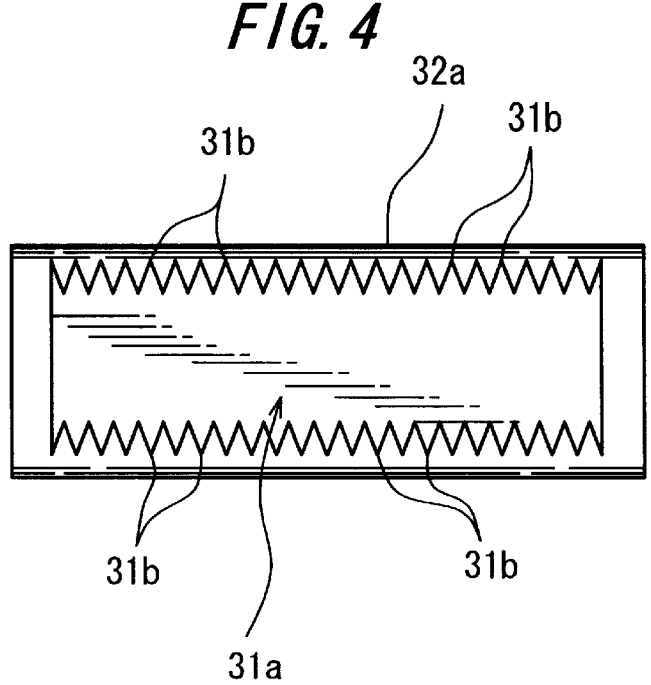
FIG. 4 is a plan view showing an ionization electrode according to the second embodiment hereof.
Figure 3:
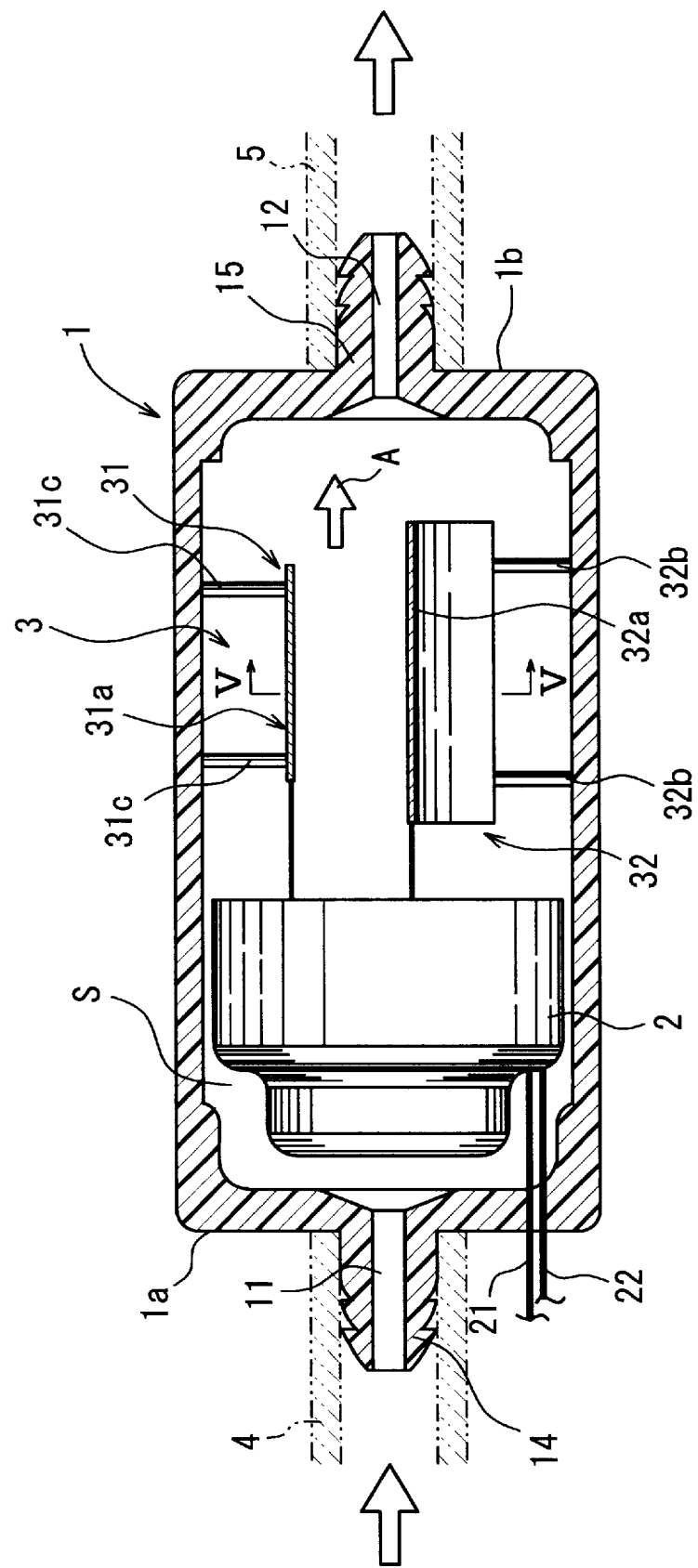
FIG. 3 is a sectional view showing an ion generator according to a second embodiment of the invention.
Figure 5:
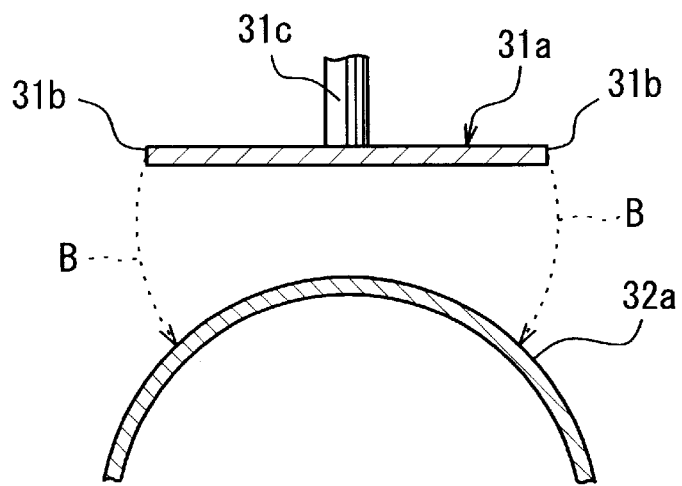
FIG. 5 is an enlarged sectional view taken on the line V—V in FIG. 3.

FIG. 3 is a sectional view showing an ion generator according to a second embodiment of the invention. FIG. 4 is a plan view showing an ionization electrode of this embodiment whereas FIG. 5 is a sectional view taken on the line V—V in FIG. 3. In the second embodiment, the ionization electrode 3 includes the positive pole portion 31 including a rectangular positive pole 31a and the support shaft 31c; and the negative pole portion 32 including a semi-cylindrical negative pole 32a and the support shaft 32b. The positive pole 31a is formed with sawtooth-like pointed ends 31b along opposite longitudinal side edges thereof. The negative pole 32a is so disposed as to have its generatrix extended in parallel with the longitudinal direction of the positive pole 31a.

Similarly to the first embodiment, the second embodiment is also arranged such that the pointed ends 31b of the positive pole 31a are not indirect face-to-face relation with the negative pole 32a and that the negative pole 32a is of a convex surface. Accordingly, the corona discharge B is prevented from concentrating on some of the pointed ends 31b due to the working errors or mounting errors of the poles. As a result, the corona discharge B occurs in a stable manner.

In the second embodiment, the positive pole 31a is formed with a large number of pointed ends 31b on the opposite ends thereof so that a large quantity of corona discharge B develop from the pointed ends 31b along the parallel longitudinal lines with respect to the positive pole 31a. This provides for an efficient air ionization and the reduction of the current value of the primary winding of the transformer to about ⅓ of that of the prior-art arrangement.

Figure 6:
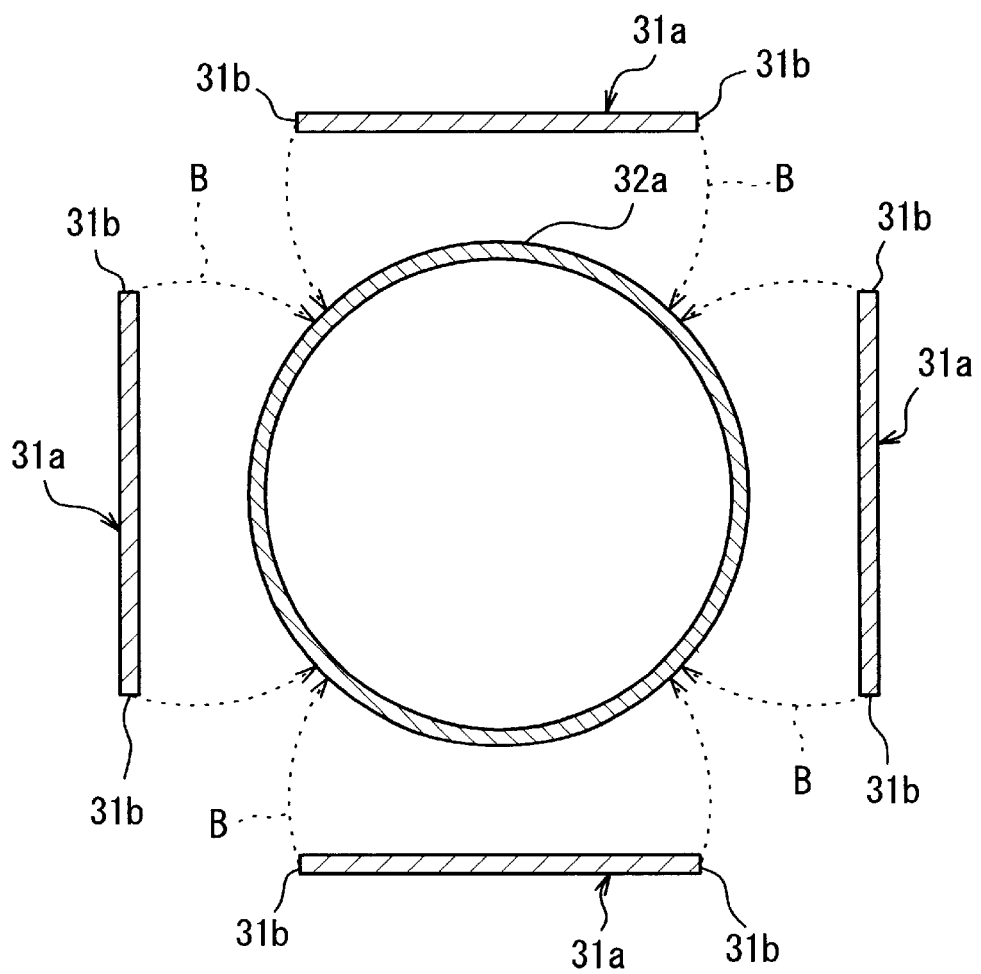
FIG. 6 is a sectional view showing an ionization electrode of an ion generator according to a third embodiment of the invention.

FIG. 6 is a sectional view showing an ionization electrode 3 according to a third embodiment of the invention. In this ionization electrode 3, a negative pole 32a is in the form of a cylinder whereas a plural number of rectangular positive poles 31a (four poles are shown in the figure) are arranged peripherally of the negative pole 32a as presenting their respective flat surfaces to a peripheral surface of the negative pole 32a, the positive pole 31a formed with the sawtooth-like pointed ends 31b on its opposite side edges as shown in FIG. 4. The ionization electrode 3 of the third embodiment is also capable of generating a large quantity of corona discharge B in a stable manner.

Figure 7:
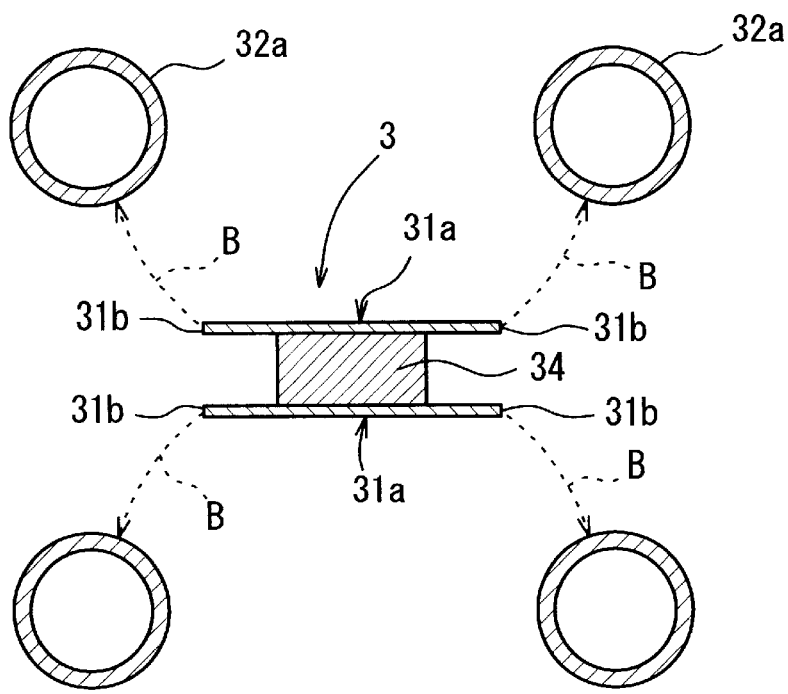
FIG. 7 is a sectional view showing an ionization electrode of an ion generator according to a fourth embodiment of the invention.

FIG. 7 is a sectional view showing an ionization electrode 3 according to a fourth embodiment of the invention. The ionization electrode 3 includes two sets of one rectangular positive pole 31a formed with the sawtooth-like pointed ends 31b on its opposite side edges as shown in FIG. 4, and a pair of cylindrical negative poles 32a, each of which is disposed in correspondence to each of the side edges of the positive pole and has a generatrix thereof extended in parallel with the corresponding pointed ends 31b. The two sets of the positive pole and negative poles are arranged in a vertically symmetrical fashion. The pair of positive poles 31a sandwich an iron plate 34 therebetween.

Similarly to the ionization electrode of FIG. 6, this ionization electrode 3 is also capable of generating a large quantity of corona discharge B in a stable manner.

Figure 8:
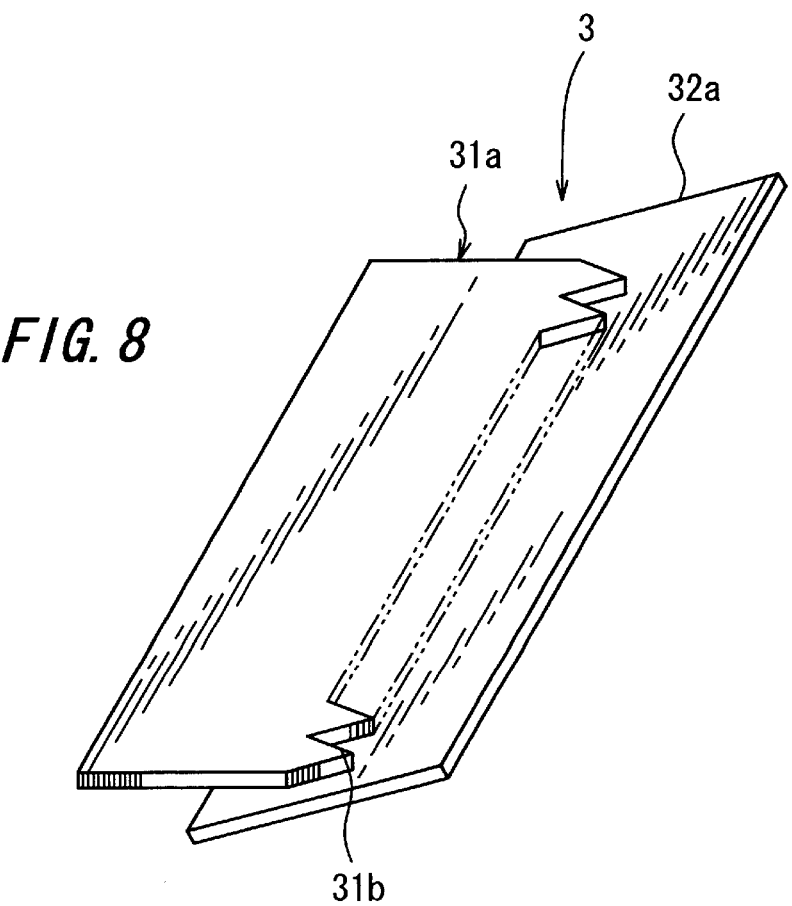
FIG. 8 is a perspective view showing an ion generator according to a fifth embodiment of the invention.

FIG. 8 is a perspective view showing an ionization electrode 3 of an ion generator according to a fifth embodiment of the invention. The ionization electrode 3 includes a rectangular positive pole 31a and a plate-like negative pole 32a opposing the positive pole 31a as inclined at a predetermined angle relative to the flat surface of the positive pole. The positive pole 31a is formed with the sawtooth-like pointed ends 31b on one longitudinal side edge thereof.

The ionization electrode 3 is also adapted to prevent the corona discharge from concentrating on some of the pointed ends 31b, thus generating a large quantity of corona discharge B in a stable manner.

Although the forgoing embodiments illustrate the ion generator having the exhaust pipe 5 communicated with the intake manifold, the invention is not limited to this arrangement. The ion generator may be incorporated in a surge-tank or the like of the intake manifold.

In correspondence to the rotational speed of an internal combustion engine or the quantity of injected fuel, the generation of the corona discharge may be controlled by giving an instruction from a computer to change a voltage value or current value for the primary winding of the transformer or by changing the position of at least one of the positive pole 31a and the negative pole 32a.

Although the foregoing embodiments illustrate the application where the ionized air is supplied to the internal combustion engine, the invention is not limited to this. The inventive ion generator may be adapted to supply the ionized air to, for example, combustion apparatuses such as boilers, incinerators and the like, deodorizers, sterilizers, air cleaners, or medical equipments designed to irradiate gangrenous area due to bacteria infection or affected area by Corixidae with ozone for treatment. Where the inventive ion generator is applied to the combustion apparatus such as a boiler, the exhaust pipe 5 of the ion generator may be communicated with an intake pipe of a burner so as to supply the air along with ozone to the burner.

Figure 9:
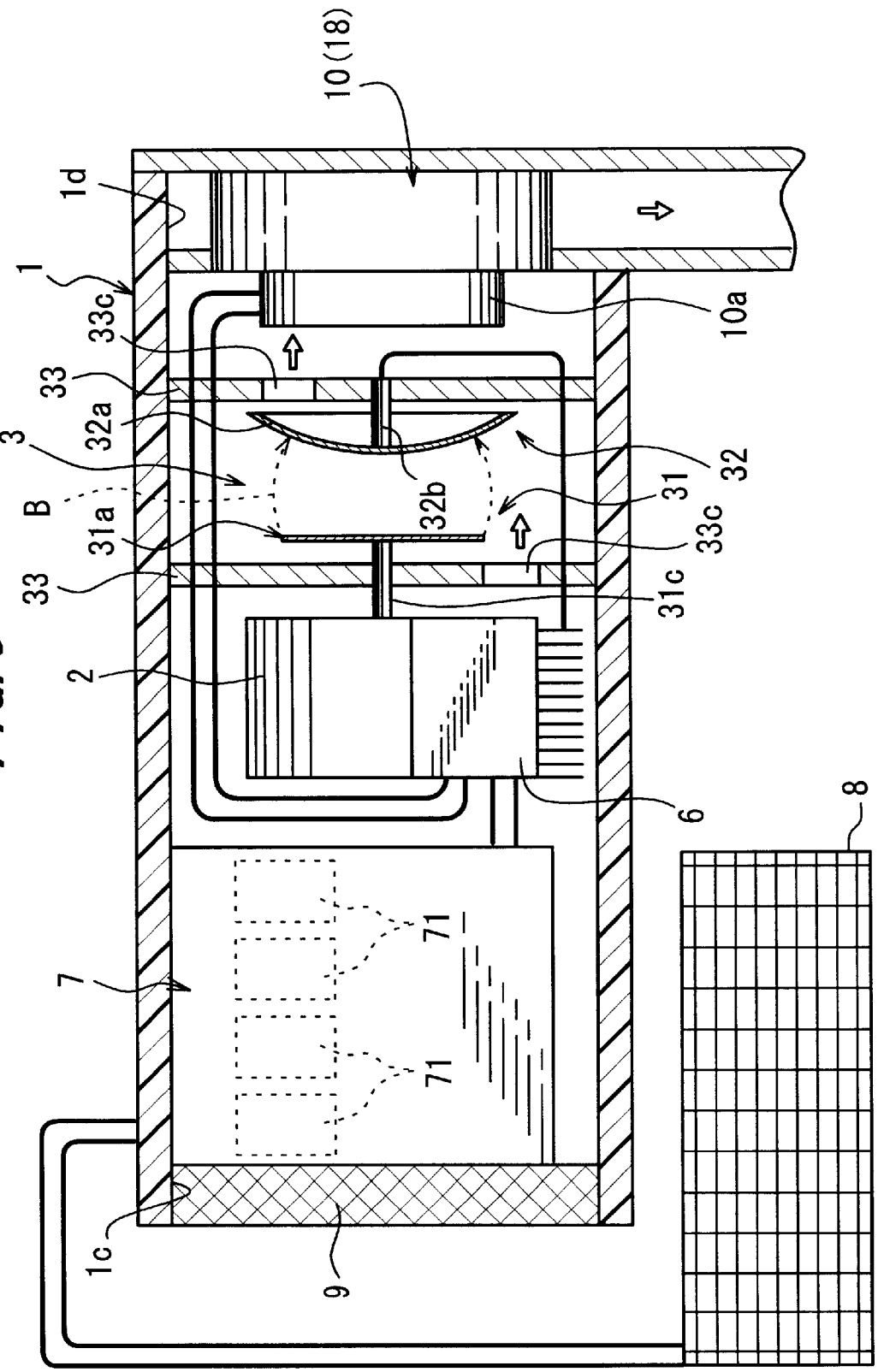
FIG. 9 is a sectional view showing an ionization electrode of an ion generator according to a sixth embodiment of the invention.
Figure 10:
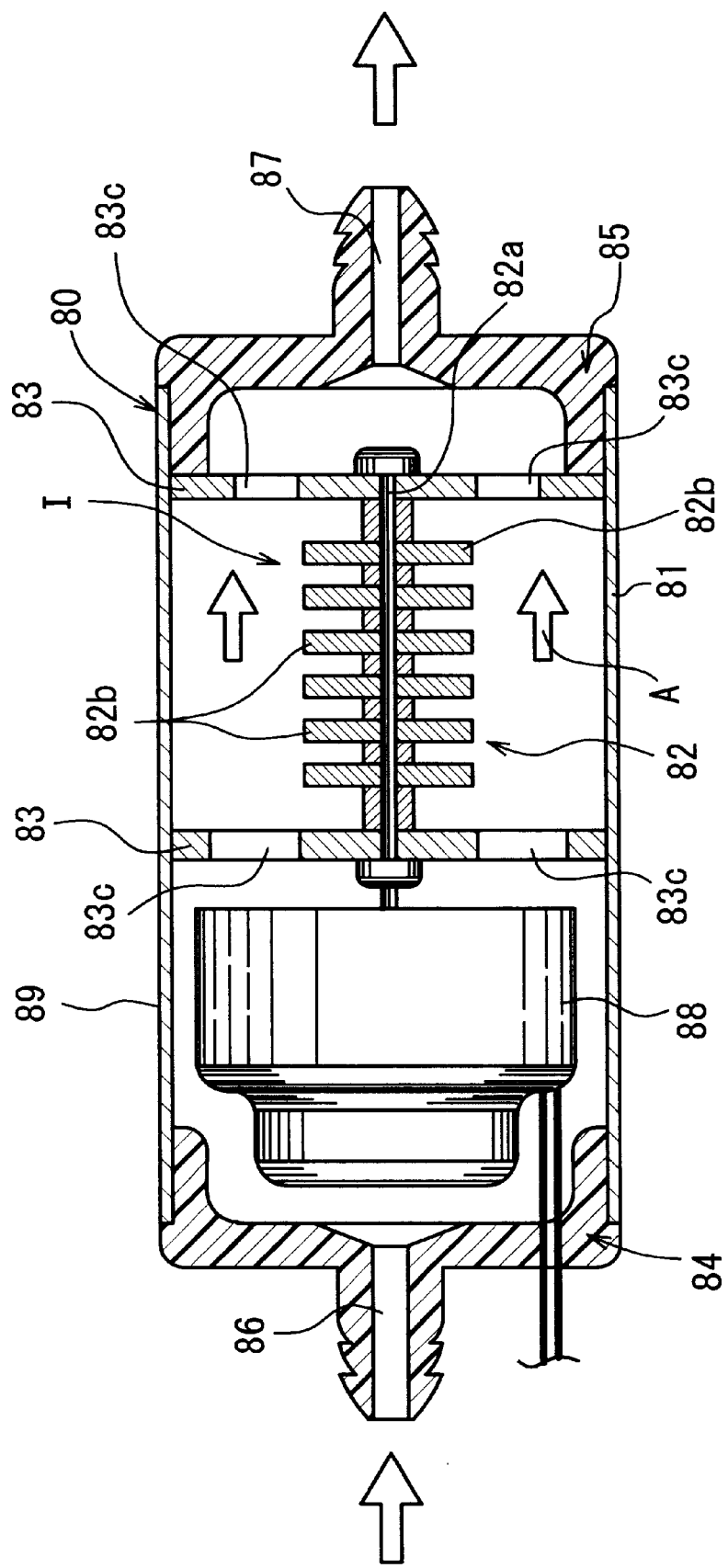
FIG. 10 is a sectional view showing a conventional ion generator.
Figure 11:
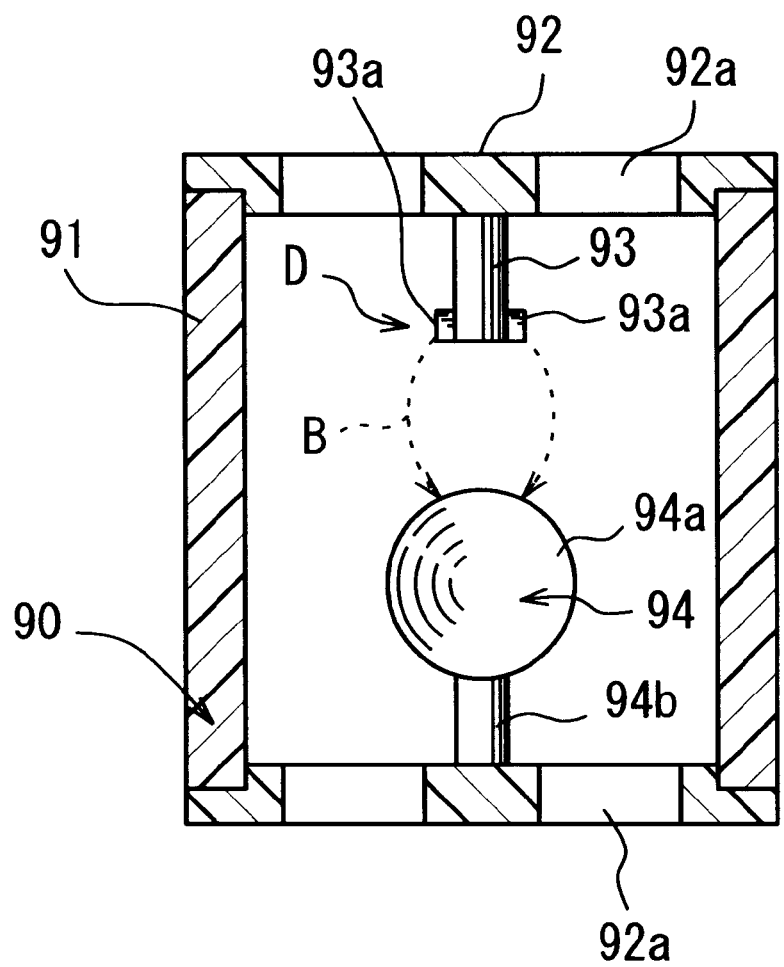
FIG. 11 is a sectional view showing an ionization electrode of another conventional ion generator.

FIG. 9 is a sectional view showing an ion generator according to a sixth embodiment of the invention. The ion generator essentially has the same arrangement as the ion generator of FIG. 1, except that the cylindrical casing 1 is provided with a dust filter 9 at one aperture 1c thereof and with a silocco fan 10 at the other aperture 1d thereof. The silocco fan 10 operates to introduce the air into the casing 1 through the dust filter 9 removing dust contained in the introduced air.

According to this embodiment, disposed in the air-flow passage A are a power source section 7, the high-voltage generator along with an electric circuit component 6, and the ionization electrode 3, the power source section located on the uppermost stream side and followed by the others in this order. The power source section 7 contains therein a plurality of storage batteries 71 which are each connected to a solar panel 8 as an external component. The solar panel 8 converts the radiation energy of the solar light to an electrical energy which is stored in the storage batteries 71. The power source section 7 is connected with the electric circuit component 6 which is connected with a power cable for a motor 10a of the silocco fan 10. The high-voltage generator 2 contains therein the electric circuit component for high-voltage generation. In addition to the storage batteries 71 for storing the electrical energy supplied from the solar panel 8, the power source section 7 may further contain therein a storage battery for storing an electrical energy supplied from an AC power source.

The above arrangement is adapted to apply a high voltage between the positive pole 31a and the negative pole 32a of the ionization electrode 3 by using the power from the storage batteries 71 of the power source section 7. Thus is generated the corona discharge between the positive and negative poles where the continuously introduced air through the dust filter 9 is ionized to generate ozone which is discharged from the casing 1 by means of the silocco fan 10.

This process generates the corona discharge B in a stable manner just as in the first embodiment, allowing for the reduction of the current value of the primary winding of the transformer and achieving an efficient air ionization. The ion generator of this embodiment uses the storage batteries 71 as the power source and hence is portable. Furthermore, the ion generator is equipped with the solar panel and designed for automatic storage of electrical energy so as to operate for an extended period of time without recharging the batteries with utility power. In this embodiment, the silocco fan 10 is provided at the aperture 1d. However, the fan at the aperture 1d may be replaced by an air pump 18.

It is noted that the ion generator of the invention is not limited to the foregoing embodiments but various changes and modifications may be made thereto within the scope of the invention. For instance, the casing 1 may be formed square in section.

An alternative arrangement may be made wherein the polarities of the positive pole 31a and the negative pole 32a are reversed so that the positive pole 31a is grounded while a negative high voltage from the high-voltage generator 2 is applied.

What is claimed is:
1. An ion generator comprising:
a casing having an intake port and an exhaust port;

an ionization electrode contained in said casing and including a first plate-like pole having a plurality of pointed ends at least on a part of its edge, and a second pole opposing a flat surface of the first pole; and a high-voltage generator for applying a high voltage to said ionization electrode, wherein said second pole has a discharge surface three-dimensionally curved into a convex surface, and wherein said first pole comprises a star electrode whereas said second pole has a spheric discharge surface.

2. The ion generator as claimed in claim 1, wherein said first pole is formed from tungsten.

3. The ion generator as claimed in claim 1, which is provided in an air charging system for supplying air to an internal combustion engine.

4. The ion generator as claimed in claim 1, wherein said intake port is provided with a dust filter whereas said exhaust port is provided with a silocco fan for discharging ionized air.

5. The ion generator as claimed in claim 1, wherein said intake port is provided with a dust filter whereas said exhaust port is provided with an air pump for discharging ionized air.

6. The ion generator as claimed in claim 1, further comprising a solar panel for converting the radiation energy of the solar light to an electrical energy, and a power source section comprising a storage battery for storing the electrical energy.

7. An ion generator comprising:

a casing having an intake port and an exhaust port;

an ionization electrode contained in said casing and including a first plate-like pole having a plurality of pointed ends at least on a part of its edge, and a second pole opposing a flat surface of the first pole; and a high-voltage generator for applying a high voltage to said ionization electrode, wherein said first pole comprises a star electrode whereas said second pole has a spheric discharge surface.

* * * * *